United States Patent
Li et al.

(10) Patent No.: US 12,245,002 B2
(45) Date of Patent: Mar. 4, 2025

(54) FITTING METHOD AND APPARATUS FOR HEARING EARPHONE

(71) Applicant: Yantao Li, Beijing (CN)

(72) Inventors: Yantao Li, Beijing (CN); Chirong Chen, Beijing (CN)

(73) Assignee: Yantao Li, Beijing (CN)

( * ) Notice: Subject to any disclaimer, the term of this patent is extended or adjusted under 35 U.S.C. 154(b) by 157 days.

(21) Appl. No.: 17/913,399

(22) PCT Filed: Dec. 16, 2020

(86) PCT No.: PCT/CN2020/136740
§ 371 (c)(1),
(2) Date: Sep. 21, 2022

(87) PCT Pub. No.: WO2021/189990
PCT Pub. Date: Sep. 30, 2021

(65) Prior Publication Data
US 2023/0111715 A1    Apr. 13, 2023

(30) Foreign Application Priority Data
Mar. 25, 2020   (CN) .......................... 202010219989.0

(51) Int. Cl.
*H04R 25/00*    (2006.01)
*A61B 5/00*    (2006.01)
(Continued)

(52) U.S. Cl.
CPC ............... *H04R 25/70* (2013.01); *H04R 3/04* (2013.01); *H04R 25/505* (2013.01);
(Continued)

(58) Field of Classification Search
USPC ..... 381/1, 2, 23.1, 303, 309, 56, 57, 58, 60, 381/61, 312, 314, 316, 317, 31, 8, 320,
(Continued)

(56) References Cited

U.S. PATENT DOCUMENTS

| 2008/0298600 A1* | 12/2008 | Poe .................. H04R 25/70 381/60 |
|---|---|---|
| 2010/0246869 A1 | 9/2010 | Zhang et al. |

(Continued)

FOREIGN PATENT DOCUMENTS

| CN | 104038879 A | 9/2014 |
|---|---|---|
| CN | 105050014 A | 11/2015 |

(Continued)

OTHER PUBLICATIONS

Chinese Patent Office Action for Related Application No. 202010219989.0 dated Jan. 4, 2021 (20 pages, including an English translation).

(Continued)

*Primary Examiner* — Qin Zhu
(74) *Attorney, Agent, or Firm* — Michael Best & Friedrich LLP (57) ABSTRACT

Disclosed are a fitting method and apparatus for a hearing earphone, which relate to the field of mobile Internet services. A specific embodiment of the method comprises: obtaining a test result of hearing threshold of a user, transmitting the test result of hearing threshold to a server, and then receiving a target compensation gain value of each of frequency bands, which value is calculated based on hearing earphone configuration information; and sending a generated pure tone signal to a hearing earphone for playing, receiving sound in an ear canal by means of an inner ear microphone arranged in the hearing earphone, so as to receive speech information generated by playing the pure tone signal, and further adjusting gain data of each of frequency bands to approximate a corresponding target compensation gain value. Therefore, the embodiments of the present invention can solve the problems of low fitting (Continued)

efficiency and reliability and high costs of existing hearing earphones.

9 Claims, 6 Drawing Sheets

(51) Int. Cl.
  *A61B 5/12* (2006.01)
  *H04R 3/04* (2006.01)
  *H04R 5/033* (2006.01)
  *H04R 29/00* (2006.01)
  *H04W 4/80* (2018.01)

(52) U.S. Cl.
  CPC ......... *H04R 25/554* (2013.01); *H04R 25/604* (2013.01); *H04R 2225/41* (2013.01); *H04R 2225/43* (2013.01); *H04R 2430/03* (2013.01)

(58) Field of Classification Search
  USPC ..... 381/74, 95, 96, 104, 107, 108, 110, 122, 381/124
  See application file for complete search history.

(56) References Cited

U.S. PATENT DOCUMENTS

| | | | | |
|---|---|---|---|---|
| 2014/0023214 A1* | 1/2014 | Edgar | .................... | H04R 25/70 381/314 |
| 2015/0016618 A1* | 1/2015 | Adachi | .................. | A61B 5/377 381/56 |
| 2015/0245150 A1* | 8/2015 | Jepsen | .................. | H04R 25/50 381/314 |
| 2015/0358745 A1* | 12/2015 | Rix | ...................... | H04R 25/305 381/60 |
| 2016/0066107 A1* | 3/2016 | Recker | ................. | H04R 25/505 463/31 |
| 2016/0249835 A1* | 9/2016 | Zhao | ...................... | A61B 5/121 600/25 |
| 2017/0164124 A1 | 6/2017 | Shennib | | |
| 2017/0230769 A1 | 8/2017 | Nguyen et al. | | |
| 2018/0242090 A1* | 8/2018 | Sigwanz | ............ | A61N 1/36039 |
| 2018/0317837 A1* | 11/2018 | Burwinkel | .............. | G06F 3/012 |
| 2019/0090073 A1* | 3/2019 | Wendt | .................... | A61B 5/125 |
| 2020/0065058 A1* | 2/2020 | Clark | ................... | H04R 1/1041 |
| 2020/0069224 A1* | 3/2020 | Perscheid | ............. | G16H 50/20 |
| 2022/0225039 A1* | 7/2022 | Huang | ................ | H04R 25/558 |

FOREIGN PATENT DOCUMENTS

| | | | | |
|---|---|---|---|---|
| CN | 105764018 A | | 7/2016 | |
| CN | 107911528 A | | 4/2018 | |
| CN | 109495833 A | | 3/2019 | |
| CN | 111447539 A | | 7/2020 | |
| EP | 1675431 A1 | | 6/2006 | |
| EP | 3062529 A1 | | 8/2016 | |
| EP | 3346732 B1 | * | 10/2020 | ............. G06F 3/162 |
| ES | 2795058 T3 | * | 11/2020 | ............. A61B 5/123 |
| WO | WO-2014183779 A1 | * | 11/2014 | ........... H04R 25/505 |
| WO | WO-2017158507 A1 | * | 9/2017 | ............. G02C 11/06 |

OTHER PUBLICATIONS

International Search Report and Written Opinion for Application No. PCT/CN2020/1367410 dated Mar. 16, 2021 (9 pages, including an English translation of the Search Report).

European Patent Office Extended Search Report and Written Opinion for Application No. 20927582.5 dated Apr. 9, 2024 (8 pages).

* cited by examiner

FITTING METHOD AND APPARATUS FOR HEARING EARPHONE

CROSS-REFERENCE TO RELATED APPLICATION(S)

This is a U.S. national stage entry of International Patent Application No. PCT/CN2020/136740, filed on Dec. 16, 2020, which claims priority to Chinese Patent Application No. 202010219989.0, filed on Mar. 25, 2020, the entire contents of each of which are fully incorporated herein by reference.

TECHNICAL FIELD

The present invention relates to the field of mobile Internet services, in particular, relates to a fitting method and device for hearing earphones.

TECHNICAL BACKGROUND

Traditional hearing earphones (which can be used as health-protect earphones, or as assistive hearing devices or hearing aids) are micro wearable devices that people usually put into their ears to help improve hearing. The foundation of correctly using of hearing equipment is (1) accurate testing of the user's hearing, including minimum hearing thresholds value and comfort hearing values, and (2) calibration of the voice values bias of the earphone equipment used during voice collection and play, which bias is caused by the electronic equipment itself. However, traditional hearing earphones need to undergo complex fitting and adjustment so as to be able to adapt to the hearing loss, behaviors and psychological characteristics for different users. Professional audiologists provide services in traditional modes, mainly through the following steps.

By professional pure tone test equipment, the user's hearing loss is tested to achieve pure tone test. According to the pure tone test results, supporting software for hearing earphone are is configured to initialize the fitting value through the fitting prescription formula, mainly for different environments, such as quiet environment, high-noise environment, outdoor environment, etc., so as to calculate gains for different frequency bands and for different bands, and at the same time to calculate Uncomfortable Loudness Level of predicted users in different frequency bands.

Hearing earphones are initialized by using the calculated value. Additional electronic earphone measuring devices are used to measure the actual gain output value of the hearing earphone. Then, the gain values of the hearing earphones are adjusted in different frequency bands and in different volumes, so that outputs of the hearing earphones are approaching to the theoretical requirement value.

Finally, the user wears the adjusted hearing earphones, simulates various voice environments by simulating the voice field in a quiet room environment, and adjusts the gain and the Uncomfortable Loudness Level of different frequency bands to make the output of the hearing earphones fit to the user's situation. In addition, in the early stage of user wearing the hearing earphones, a regular return visit is necessary so that the user need to return to the hearing fitting center regularly to make adjustments to hearing earphones better fitting the user's situation. In this process, two main voice problems need to be solved, one is the adjustment of the user's hearing comfort level threshold, and another one is the calibration of the voice error of the hearing earphone itself as an electronic device.

In the process of realizing the present invention, the inventor found that there are at least the following problems in current existing technologies.

The current fitting process for hearing earphones not only requires the hearing aids to have strong professional skills, but also requires professional equipment and venues so as to carry out the fitting operations. Therefore, the fitting efficiency for the hearing earphone is extremely low, and the accuracy is difficult to be controlled, and the users' satisfaction of the fitting for the hearing earphone is always low. In addition, the service cost of hearing earphone providers is high, which pushes up the cost of hearing earphones for customers, making it more difficult to accept hearing earphones.

SUMMARY

In view of this, the embodiments of the present invention provide a fitting method and device for hearing earphones, which can solve the existing problems of low fitting efficiency, low reliability and high cost of hearing earphones.

In order to achieve the above objectives, according to one aspect of the embodiments of the present invention, a fitting method is provided for hearing earphones, which includes:

obtaining a test result of a user's hearing threshold to transmit a test data of the hearing threshold to a server, thereby receiving target compensation gain values of each of frequency bands calculated based on configuration information of the hearing earphone;

sending pure tone signals as generated to the hearing earphone to play the generated pure tone signals, and receiving sound in an ear canal by an inner ear microphone built in the hearing earphone so as to receive voice information after playing the pure tone signal, and thereby to adjust gain value data of each of frequency bands to approach corresponding target compensation gain values.

Optionally, the method further includes:

obtaining and sending different types of voice information in a quiet environment to the hearing earphone to play the different types of voice information, receiving the sound in the ear canal by the inner ear microphone built in the hearing earphone so as to receive a selected type of voice information, wherein, the different types of voice information are a combination of sounds at different frequency points;

recurrently performing a procedure in which the gain data after adjustment at each of frequency bands is re-adjusted based on the selected type of voice information, the re-adjusted gain data at one of frequency bands is selected as output gain data, and the output gain data is sent to the hearing earphone, until a voice confirmation instruction is received.

Optionally, the method further includes:

obtaining and sending the voice information under different types of noise environments to the hearing earphone, playing the voice information under each of the noise environments in a manner of adjusting the gain values of high frequency, of medium frequency or of low frequency respectively, and receiving sound in the ear canal by the inner ear microphone built in the hearing earphone;

receiving a selected manner of adjustment for each of the noise environments, and thereby recurrently performing a procedure including adjusting the re-adjusted gain data of each of frequency bands, selecting the re-adjusted gain data of one frequency band as the output gain data, and sending the output data to the hearing earphone until the voice confirmation instruction is received.

Optionally, the method further includes:

sending a voice data request to the server, and obtaining the voice information under a quiet environment or the voice information under different types of noise environment, which are stored in the server.

Optionally, the method further includes:

by a pure tone generator and a narrow-band noise generator, generating a pure tone signal and a narrow-band noise signal, respectively;

synthesizing the pure tone signal and the narrow-band noise signal for voice playing, and setting a preset volume, thereby sending the pure tone signal and the narrow-band noise signal to the hearing earphone to play the narrow-band noise signal so as to perform the test of the user's hearing threshold.

Optionally, the method further includes:

encoding the generated pure tone signal, and sending the encoded pure tone signal to a Bluetooth communication module in the hearing earphone, playing the encoded pure tone signal after being processed by a voice processing and amplifying module in the hearing earphone, recording the played voice by a microphone built at the frontend of a transmitter, and receiving the voice information encoded by the Bluetooth communication module.

Besides, the present invention further provides a fitting device for a hearing earphone, including:

pure tone testing module which is configured to obtain a test result of a user's hearing threshold; and gain testing module which is configured to transmit the test result of the user's hearing threshold to a server, to receive target compensation gain values of each of frequency bands calculated based on configuration information of the hearing earphone, to send pure tone signals as generated to the hearing earphone to play the pure tone signals, and to receive sound in an ear canal by an inner ear microphone built in the hearing earphone so as to receive voice information after playing the pure tone signal, and thereby to adjust gain value data of each of frequency bands to approach corresponding target compensation gain values.

Optionally, the device further includes an ambient voice testing module which is configured to obtain and send different types of voice information in a quiet environment to the hearing earphone to play the different types of voice information, to receive the sound in the ear canal by the inner ear microphone built in the hearing earphone so as to receive a selected type of voice information, wherein, the different types of voice information are a combination of sounds at different frequency points, wherein, a procedure in which the gain data after adjustment at each of frequency bands is re-adjusted based on the selected type of voice information, the re-adjusted gain data at one of frequency bands is selected as output gain data, and the output gain data is sent to the hearing earphone, is recurrently performed, until a voice confirmation instruction is received.

An embodiment of the above invention has the following advantages or beneficial effects. In particular, the test result of the user's hearing threshold is obtained, the test result of hearing threshold is transmitted to the server, and then the target compensation gain value of each frequency bands calculated based on the configuration information of the hearing earphone is received. The pure tone signal is sent to the hearing earphone for playing, and the inner ear microphone built in the hearing earphone receives the sound in the ear canal to receive the sound information after playing the pure tone signal, and then adjusts the gain data of each of frequency bands to approach the corresponding target compensation gain values. As such, the existing technical problems of low fitting efficiency and reliability and high cost for hearing earphones are overcome. The fitting efficiency and reliability of hearing earphones are improved, the cost of hearing services is reduced, and the coverage of hearing services is improved.

Further effects of the above-mentioned non-traditional alternatives will be described below in conjunction with specific embodiments.

DRAWINGS OF THE DESCRIPTION

The accompanying drawings are used for better understanding of the present invention and do not constitute an improper limitation of the present invention. Herein.

SPECIFIC MODE OF CARRYING OUT THE INVENITON

Exemplary embodiments of the present invention are described below with reference to the accompanying drawings, which include many details of the embodiments of the present invention to facilitate understanding, should be considered as exemplary only. Accordingly, those people of usual technical skills should recognize that various changes and modifications of the embodiments described herein can be made without departing from the scope and spirit of the invention. Also, descriptions of well-known functions and constructions are omitted from the following description for clarity and conciseness purpose.

Figure 1:
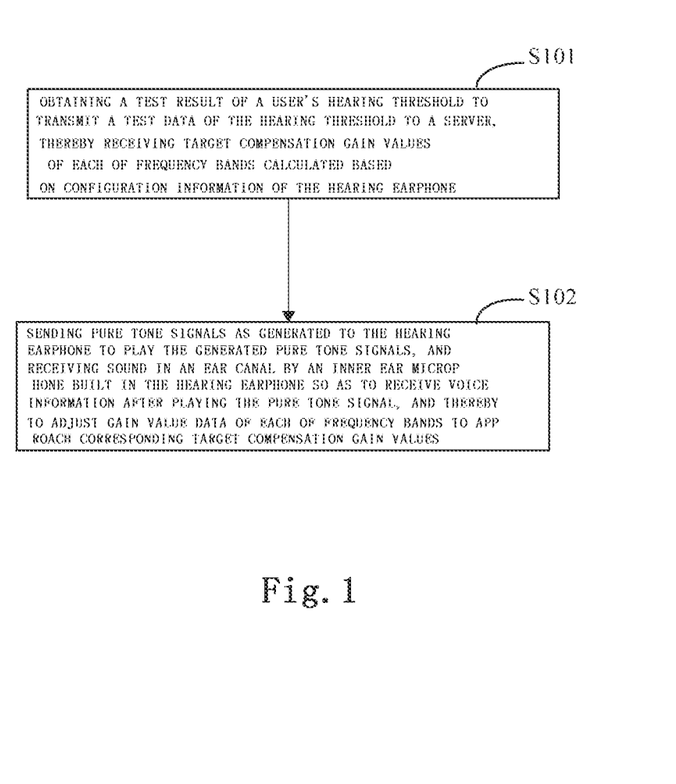
FIG. 1 is a schematic diagram of the main flow of a fitting method for a hearing earphone according to the first embodiment of the present invention.

FIG. 1 is a schematic diagram of the main flow of a fitting method for a hearing earphone according to a first embodiment of the present invention. As shown in FIG. 1, the fitting method for a hearing earphone includes:

Step S101, acquire the test result of hearing threshold of the user, so as to transmit the test result of hearing threshold to the server, and then receive the target compensation gain value of each of frequency bands calculated based on the configuration information of the hearing earphone.

Herein, hearing earphones refer to hearing assistive devices with frequency division compensation ability, which include health earphones, hearing assistive earphones, and hearing aids, and other common hearing compensation devices.

In some embodiments, after the test of hearing threshold is completed, the results of the test of hearing threshold (such as the user's minimal audible threshold and hearing comfort zone maximum value) are transmitted to cloud server at the backend. The cloud platform server calculates the gain value to be compensated in each frequency band according to the user's hearing threshold and the configuration information of the hearing earphones, and transmits the calculation result to the terminal application software, which transmits the same with the data format of the hearing earphones to the hearing earphones.

That is to say, through the pure tone test (that is, the test of hearing threshold), the minimum audible hearing threshold of the user (that is, the test result of hearing threshold) is obtained. Then, the hearing compensation gain value (that is, the target compensation gain value) is obtained through calculation by the server, and the sound compensation for the hearing of the user is made. Herein, the target compensation gain value calculated by the server is obtained by applying the user's hearing loss value (the user's minimum hearing threshold value) to the hearing prescription, wherein the hearing prescription is an acoustics curve model obtained through group statistics.

Then, the error of amplification volume the hearing earphone needs to be corrected to ensure that the gain output from the hearing earphone is the target compensation gain value, that is, step S102 is performed.

As a preferred embodiment, the user test result of hearing threshold can be obtained through the following process, which specifically includes:

entering the test of hearing threshold through the self-fitting software interface of user-end, generating pure tone signal and narrow-band noise signal respectively by means of a pure tone generator and a narrow-band noise generator, synthesizing the pure tone signal and the narrow-band noise signal for voice playing, setting a preset volume, and then sending the same to the hearing earphone for playing so as to perform the test of hearing threshold.

The user's testing process starts with a single-frequency signal of 1 kHz, to test the user's minimal audible hearing threshold and the maximum value of the hearing comfort zone, followed by 2 kHz, 4 kHz, and 8 kHz. If the difference between the last frequency point and the current test frequency point is greater than 15 dB, 3 kHz, 6 kHz and other frequency test points could be added in the middle. After testing 8 kHz, it is verified whether the 1 kHz test is accurate. If the difference between the last frequency point and the current test frequency point is greater than 5 dB, the test could be restarted. If the difference between the last frequency point and the current test frequency point is less than 5 dB, the low frequency signals of 500 Hz, 250 Hz and 125 Hz could be started to test.

It is worth noting that, before the test of hearing threshold, the user can download the end-user application software in a preferable way, install and run the software. After the Bluetooth hearing earphones is turned on, the end-user application software is connected through Bluetooth to test the level of ambient noise and remind the users whether fitting requirements are satisfied. (test environment requirements, specified in the test GB-T16296-1996, should be below 35 dB SPL) so as to reduce the impact of environmental noise.

As another embodiment, when step S101 is performed, the generated pure tone signal can be encoded and be sent to the Bluetooth communication module in the hearing earphone. The voice information can be obtained by playing and recording through the microphone at the front end of the microphone in the hearing earphone, to receive the voice information encoded by the Bluetooth communication module.

At Step S102, the generated pure tone signal is sent to the hearing earphone for playing. The sound in the ear canal through the inner ear microphone (the microphone at the front end of the microphone) built in the hearing earphone is received, so as to receive the voice information after playing the pure tone signal. Then, the gain data of each of frequency bands is adjusted to approach the corresponding target compensation gain values.

As an example, due to differences in sound produced by the different types of hardware of the hearing earphones, the sounds finally produced by the hardware are also different for the same hearing compensation data. During fitting process, the present invention uses the inner ear microphone built in the hearing earphone to directly test the human ear environment and calibrate the output sound value. That is to say, the present invention adopts a brand-new method, directly on the hearing earphone, and specially builds a microphone facing the inner ear canal in front of a transmitter, directly measures the sound pressure of the inner ear canal, and then calibrates and compensates the sound of the earphone according to the sound result. Herein, the auditory measurement microphone for internal ear canal has been calibrated and tested when it is produced from factory, and the test data is stored in the background server and hearing earphones, so that the accuracy of the sound pressure during user testing is guaranteed.

Therefore, the present invention eliminates the need to use another audiometer to perform manual test, i.e., artificial ear test, and to calibrate the output in the prior art. Moreover, the present invention no longer requires a professional mute room and expensive audiometric instruments, rather replaces a professional mute room by a user's selection of a quiet environment and using a hearing earphone by the user. Through the hearing earphone hardware and the corresponding APP software in a mobile phone, the testing and calibration of each hearing earphone can be carried out in an automatic or a DIY way. To sum up, the hearing fitting of the present invention does not require professional instruments, operators and a mute room environment, accordingly greatly saves the cost of fitting, and also makes the whole process of remote and DIY fitting into reality.

In a specific embodiment, taking 1 kHz as an example, a pure tone of 1 kHz is played into the hearing earphone. After the pure tone sound being amplified in the hearing earphone, it is played through the speaker. The microphone in front of the speaker receives the sound in the ear canal, and then receives the actual sound pressure value, compares the required sound pressure value, and adjusts the target gain value until the measured sound pressure matches the required sound pressure. If the sound pressure is less than 1 dB, the 1 kHz test can be completed. The other frequency point tests are carried out in sequence to complete the full-band correction.

In the prior art, the hearing adaptation formula curve (referred to as the audiogram curve) adopted by hearing research institutions or hearing commercial companies is based on statistical simulations made by some people. Since the hearing curve is a statistical model, the generated statistical value is not good for more than 80% of users. Therefore, as a preferred embodiment, the present invention makes modifications for individuals. That is to say, each person has a different perception of sound loudness, and the responsiveness of different environments is also different. Fine adjustment can be performed, including the user's own preferred perception of the voice (such as sound volume, preference for high frequency or low frequency) and the user's own preference for voice in different ambient sound fields.

In a further embodiment, when considering the user's own preference for hearing sound, the minimum audible value that the user can hear is different from the user's hearing comfort value. Everyone's perception of sound loudness is a psychological factor, so for different person, there is a difference in the amount of sound energy heard and the distribution of sound at high and low frequencies. And, the loudness compensation of hearing earphones needs to be adjusted for each person. For example, if the user likes the sound to be louder, more gain is required for the mid-frequency, and the high-frequency gain needs to be moderately reduced. If the user likes a soft and natural sound, it is necessary to increase the high frequency gain and moderately reduce the low frequency gain. That is to say, different kinds of voice information (such as soft and natural voice) can be obtained by adjusting the target gain of intermediate frequency, high frequency and low frequency in a quiet environment, for the user to choose the preferred voice information, and then fine-tune the voice based on the selected voice information.

Specifically, it includes: obtaining different types of voice information in a quiet environment and sending them to the hearing earphones for playback (that is, playing different sounds so that user can select favorite sounds), and receiving the sounds in the ear canal through the inner ear microphone built in the hearing earphones so as to receive the type of voice information selected, so as to understand the user's sound comfort zone of hearing. Further, the adjusted gain data of each of frequency bands is re-adjusted based on the selected type of the voice information, and then the gain data of one frequency band after the readjustment is selected as the output gain data and sent to the hearing earphone. It is determined whether a voice confirmation instruction is received. If so, the program would be ended. If not, it will continue to re-adjust the adjusted gain data of each of frequency bands based on the voice information of the selected type, select the gain data of the re-adjusted frequency band as the output gain data, and send it to hearing earphones, until a voice confirmation instruction is received. Herein, the different types of voice information are a combination of sounds at different frequency points.

In addition, in the process of determining the user's own preference of voice of different environments, the voice of different noise environments can be played, and the voice adjustment in different noise environments can be completed by adjusting the gain of mid frequency, high frequency and low frequency. This is because, in a noisy environment, the AC volume is too large, and the results of sound comfort in different noise environments are also different. Such environments are like, for example, low noise environment, high noise environment, outdoor environment, quiet office environment and other scenarios.

Specifically, it includes: obtaining voice information under different types of noise environments, and sending them to the hearing earphones, playing the voice information under each noise environment by adjusting the high-frequency, mid-frequency or low-frequency gain values respectively, and using the inner ear microphone built in the hearing earphones to receive sound in the ear canal. The adjustment manner for each selected noise environment (so as to understand the user's hearing comfort zone in different types of noise environments) is received. Further, the re-adjusted gain data of each of frequency bands is adjusted based on the selected adjustment manner under each noise environment, and the gain data of one frequency band after the re-adjustment is selected as output gain data and sent to the hearing earphone. It is determined whether a voice confirmation instruction is received. If so, it will end the program. If not, it will continue to adjust the re-adjusted gain data of each of frequency bands based on the selected adjustment manner under each noise environment, and select the adjusted gain data of a frequency band as the output gain data, and send it to the hearing earphone, until the voice confirmation instruction is received, and finally the gain data under different types of noise environments are obtained.

It should be noted that the voice information stored in the server in a quiet environment or voice information in different types of noise environments can be obtained by sending a voice data request to the server.

Figure 2:
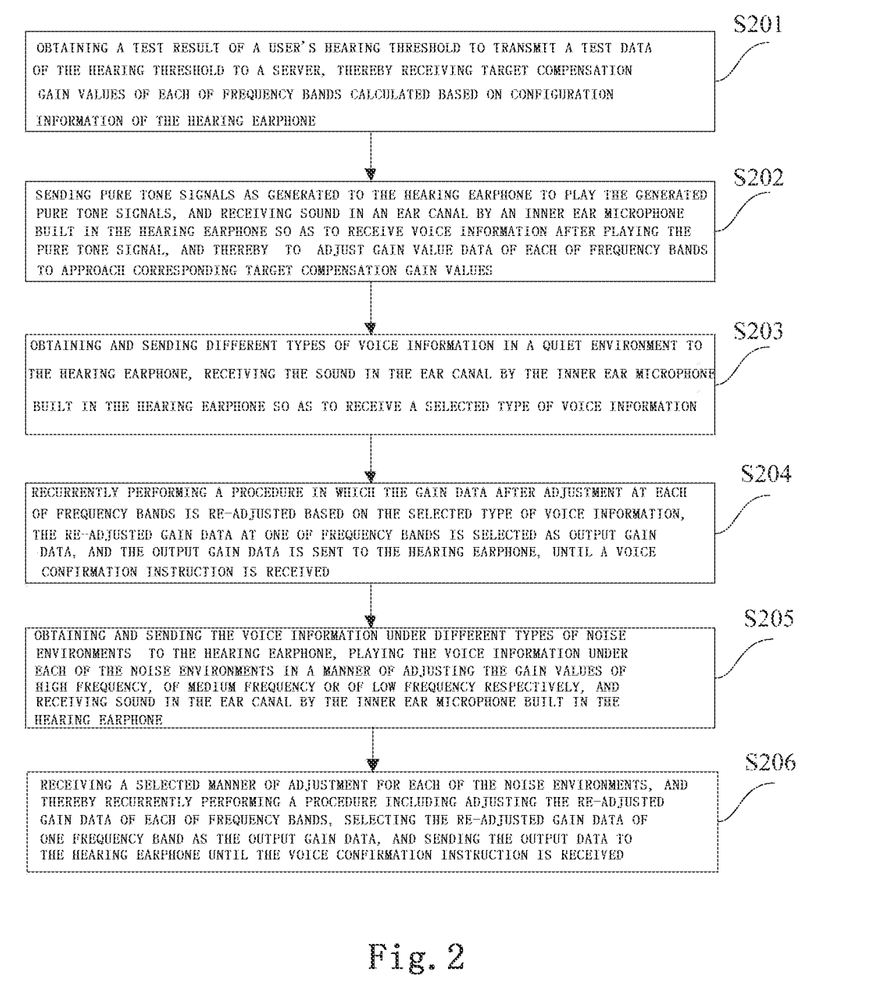
FIG. 2 is a schematic diagram of the main flow of the fitting method for a hearing earphone according to the second embodiment of the present invention.

FIG. 2 is a schematic diagram of the main flow of a fitting method for a hearing earphone according to a second embodiment of the present invention. As shown in FIG. 2, the fitting method for a hearing earphone includes:

Step S201, it acquires the test result of hearing threshold of the user, so as to transmit the test result of hearing threshold to the server, and then receive the target compensation gain value of each of frequency bands calculated based on the configuration information of the hearing earphone. Step S202, the generated pure tone signal is sent to the hearing earphone for playback, and the inner ear microphone built in the hearing earphone receives the sound in the ear canal to receive the sound information after the pure tone signal is played, and then adjusts the gain data of each of frequency bands to approach the corresponding target compensation gain values.

In some embodiments, when adjusting the gain data of each of frequency bands to approach the corresponding target compensation gain value, it can be determined whether the error with regard to the corresponding target compensation gain value is less than a preset error threshold (for example, the error threshold is 1 dB). If so, the adjustment is completed. Otherwise, it will continue to adjust until it is less than the preset error threshold. Therefore, at step S202, it is mainly to correct the errors resulting from the sound playing and sound receiving of the electronic device.

Step S203: obtaining different types of voice information in a quiet environment and send them to the hearing earphone for playback, and receiving the sound in the ear canal through the inner ear microphone built in the hearing earphone to receive the selected type of voice information.

Step S204: recurrently performing re-adjustment of the adjusted gain data of each of frequency bands based on the selected type of voice information, selecting the gain data of the re-adjusted frequency band as the output gain data, and sending it to the hearing earphone, until the voice confirmation instruction is received.

Herein, S203 and S204 mainly test the user's hearing comfort zone value in a quiet environment.

Step S205: obtaining sound information under different types of noise environments to send to the hearing earphones, playing the voice information under each noise environment by the way of adjusting the high-frequency, mid-frequency or low-frequency gain values respectively, receiving sound in the ear canal through the inner ear microphone built in the hearing earphones.

Step S206: receiving the selected adjustment manner under each noise environment, and then recurrently performing the adjustment of the re-adjusted gain data of each of frequency bands, selecting the gain data of a frequency band after adjustment as the output gain data, and sending it to the hearing earphone, until the voice confirmation instruction is received.

Herein, S205 and S206 mainly test the user's hearing comfort zone value in different sound fields or different noise environments.

To sum up, the fitting method for hearing earphones of the present invention relates to the fields of mobile phones, the Internet, artificial intelligence and medicine hearing, etc. The Internet and artificial intelligence can be used to improve the ability of hearing earphones, so that hearing impairment people can get normal communication under different noise backgrounds with guarantee. Also, the fitting method of the present invention can be used for the normal hearing persons to customize their earphones sound playing configuration under normal sound environment and under different noise environments. Moreover, by improving the hearing earphones fitting process, the present invention supports autonomous fitting, simplifies the human's work skills for hearing aid services, and reduces the cost of hearing aid services while improving the effectiveness of fitting.

Figure 3:
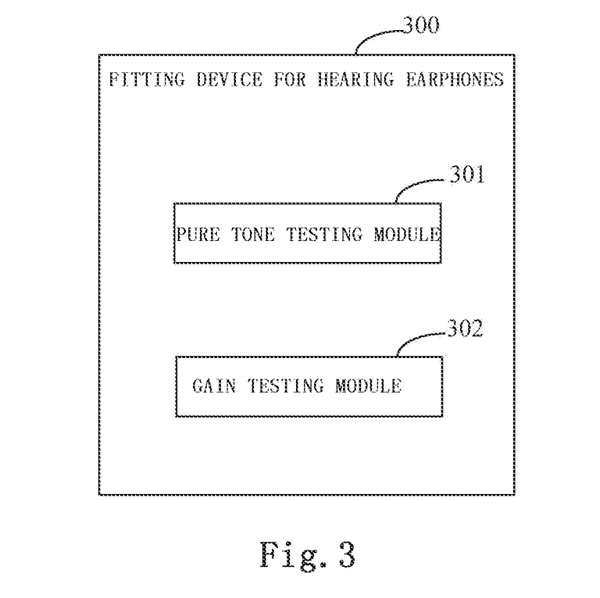
FIG. 3 is a schematic diagram of the main modules of the fitting device for a hearing earphone according to the first embodiment of the present invention.

FIG. 3 is a schematic diagram of main modules of a fitting device for hearing earphones according to an embodiment of the present invention. As shown in FIG. 3, the fitting device 300 for hearing earphones includes a pure tone testing module 301 and a gain testing module 302. Herein, the pure tone testing module 301 obtains the test result of the user's hearing threshold. The gain testing module 302 transmits the test result of hearing threshold to the server, and then receives the target compensation gain value of each of frequency bands calculated based on the hearing earphone configuration information; and sends the generated pure tone signal to the hearing earphone to play the generated pure tone signal, receive the sound in the ear canal through the inner ear microphone built in the hearing earphone to receive the sound information after the pure tone signal is played, and then adjust the gain data of each of frequency bands to approach the corresponding target compensation gain value.

Figure 4:
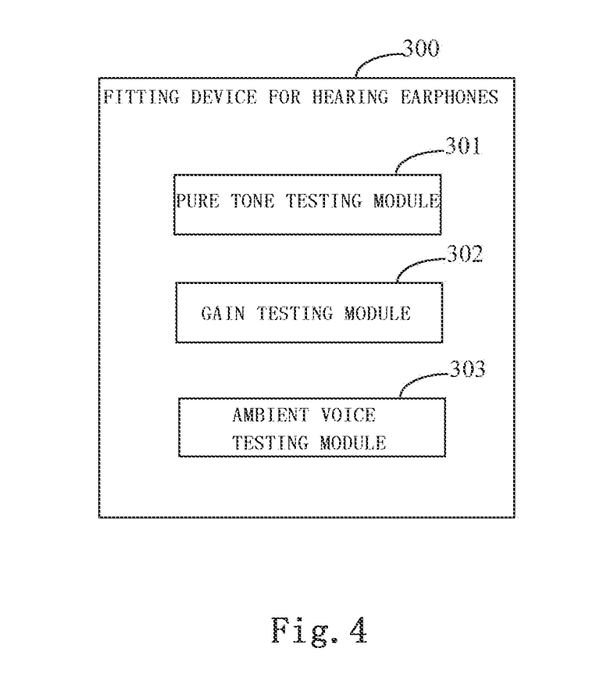
FIG. 4 is a schematic diagram of the main modules of the fitting device for a hearing earphone according to the second embodiment of the present invention.

In some embodiments, as shown in FIG. 4, the fitting device 300 for a hearing earphone includes a pure tone testing module 301, a gain testing module 302 and an ambient voice testing module 303. Herein, the pure tone testing module 301 obtains the test result of user's hearing threshold. The gain testing module 302 transmits the test result of hearing threshold to the server, and then receives the target compensation gain value of each of frequency bands calculated based on the hearing earphone configuration information. It sends the generated pure tone signal to the hearing earphone to play the generated pure tone signal, receives the sound in the ear canal through the inner ear microphone built in the hearing earphone, to receive the information after the pure tone signal is played, and then adjusts the gain data of each of frequency bands to approach the corresponding target compensation gain value. The ambient voice testing module 303 obtains the quiet environment so as to send the different types of voice information to the hearing earphones for playing. The sound in the ear canal is received by the inner ear microphone built in the hearing earphones, so as to receive the type of the selected voice information, wherein, the different types of voice information are a combination(s) of voices of different frequencies. It recurrently executes a procedure of re-adjusting the adjusted gain data of each of frequency bands based on the voice information of the selected type, selecting the gain data of the re-adjusted frequency band as the output gain data, and sending it to the hearing earphone, until the voice confirmation instruction is received.

In some embodiments, the ambient voice testing module 303 is also is configured to:

acquire the voice information under different types of noise environments to send to the hearing earphones, play the voice information under each noise environment by adjusting the gain value of high frequency, medium frequency or low frequency respectively, and receive the voice of inner ear microphone through the inner ear microphone built in the hearing earphones; and receive the selected adjustment manner under each noise environment, and then recurrently execute the adjustment of the re-adjusted gain data of each of frequency bands, selecting the gain data of the re-adjusted frequency band as the output gain data, and sending it to the hearing earphone program, until the voice confirmation instruction is received.

In some embodiments, the ambient voice testing module 303 is further configured to:

send a voice data request to the server, and obtain voice information stored in the server in a quiet environment or voice information in a different type of noise environment.

In some embodiments, before the pure tone testing module 301 obtains the test result of user's hearing threshold, it includes that:

by the pure tone generator and the narrow-band noise generator, the pure tone signal and the narrow-band noise signal are generated respectively; the pure tone signal and the narrow-band noise signal are synthesized for voice playback, and the preset volume is set, and then sent to the hearing earphone for playback to perform the test of hearing threshold.

It should be noted that the fitting method for a hearing earphone and the fitting device for a hearing earphone of the present invention have a corresponding relationship in the specific implementation contents, so the repeated contents will not be described again.

Figure 5:
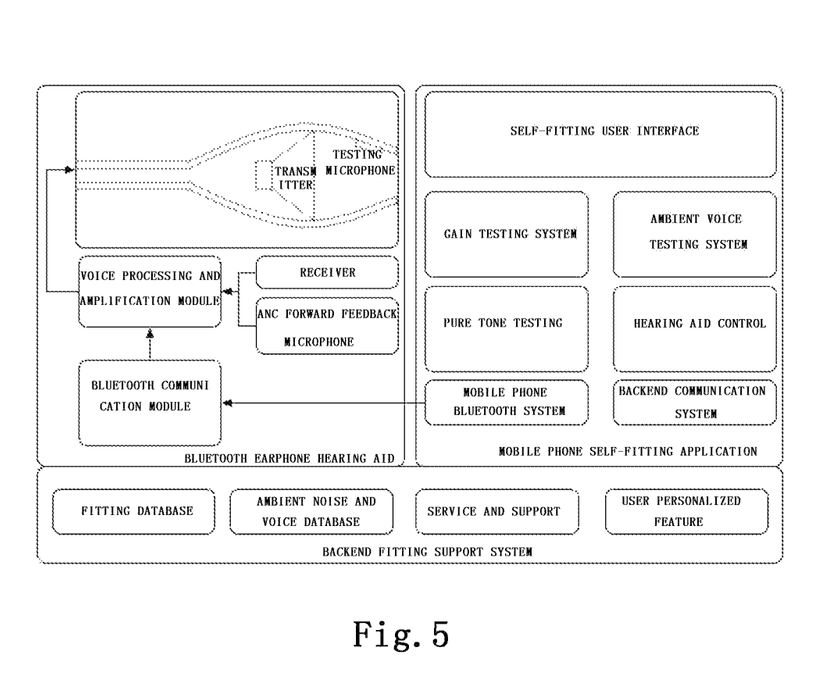
FIG. 5 is a schematic diagram of the main modules of the fitting device for a hearing earphone according to the third embodiment of the present invention.

As another embodiment, as shown in FIG. 5, a self-fitting application software is based on a mobile phone. Herein, the self-fitting user interface is configured to interact with the user, in addition to the display module, including pure tone testing module, gain testing module, ambient voice testing module, hearing earphone control (such as the hearing aid control in the figures), mobile phone Bluetooth system and backend communication system.

The mobile phone Bluetooth system can communicate with the Bluetooth communication module of the Bluetooth-based hearing headphone (such as the Bluetooth earphone hearing aid in the figures), so as to realize the connection between the self-fitting application software on mobile phone and the Bluetooth hearing earphone. The backend communication system can realize the communication between the mobile phone self-fitting application software and the platform server in the cloud (for example, the backend fitting support system in the figures).

In addition, as a specific embodiment of the present invention, a client's software APP (such as a mobile phone) can be used to connect a hearing earphone including a Bluetooth communication module, and by improving the structure of the hearing earphone, the fitting process for the hearing earphone can be simplified, so that self-fitting is possible. Further, the hearing earphone supports general Bluetooth protocols such as Bluetooth A2DP (Advanced Audio Distribution Profile), SCO (Synchronous Connection Oriented), HFP (Hands-Free Profile), and users can directly use the hearing earphone as a Bluetooth earphone to make calls, listen to music, and support the HAP (HomeKit Accessory Protocol) for hearing earphones. Therefore, the hearing earphone supports playing different sounds through the mobile phone software, and can control the volume of the playing sound through the software.

Preferably, a Bluetooth communication module is built in the hearing earphone, and its voice is output to the transmitter through the voice processing and amplification module, so as to compensate the hearing loss. It should be noted that the voice processing and amplification module included in the hearing earphone can receive the voice from the receiver (that is, the sound-collecting microphone of the hearing earphone), and perform voice processing (noise reduction, echo processing, encoding and decoding) and compression and amplification (the parameters of its compression and amplification come from the HAP protocol).

In addition, the hearing earphone has a built-in microphone facing the inner ear and located in the front of the speaker of the hearing earphone. The microphone can be used for the backward feedback of ANC (Active Noise Cancellation) when in use, and the Active Noise Cancellation can reduce the user's ear blocking effect. The ANC basically uses the direction of ANC forward feedback microphone to achieve the noise cancellation of inner ear noise. That is, the microphone exists as a test sensor for testing the output sound pressure, avoiding the use of electronic ears, and can accurately measure the actual value of the output, that is, the microphone is used to test the sound pressure of the output voice to correct the fitting bias.

In addition, the platform server in the remote cloud (for example, the backend fitting support system in the figures) may include a fitting database that stores various data of the fitting process, an ambient noise and voice database which stores voice information in a quiet environment or voice information in different types of noise environments, a service and support module that provides various services, and a user personalized feature module for some personalized services.

Figure 6:
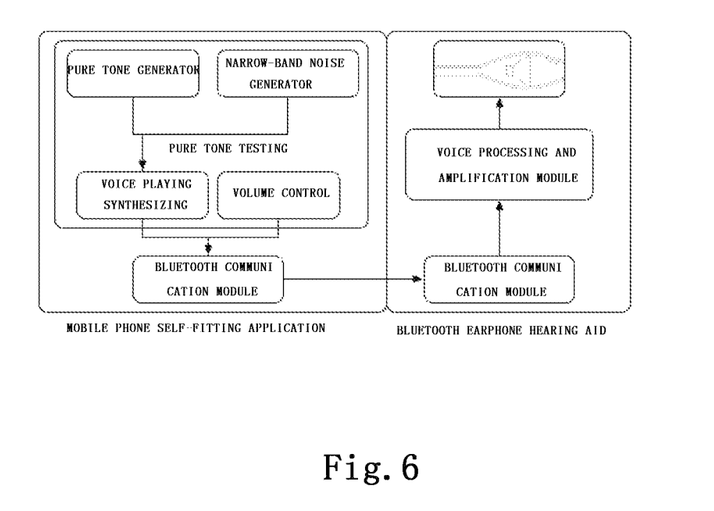
FIG. 6 is a schematic diagram of performing a test of hearing threshold by a pure tone testing module according to an embodiment of the present invention.

In a further specific embodiment, the pure tone testing module, as shown in FIG. 6, supports the pure tone test of GB-T16296-1996 to determine the user's hearing threshold. The module generates pure tone signals and narrow-band noises respectively through a pure tone generator and a narrow-band noise generator. The noise signal is then processed by voice playing synthesizing and volume controlling to process the pure tone signal and the narrow-band noise signal, and play it to the user through a hearing earphone (such as the Bluetooth hearing aid in the picture). Herein, the voice playing synthesizing is to put the generated voice signal data into the left and right channels to synthesize the playback stream. Voice Control is a controlling of volume, that is, to obtain a sound of a specific volume. Since it is transmitted through the Bluetooth communication module, encoding and decoding processing is required. During the pure tone test, the voice processing and amplifying modules in the hearing earphones do not work except for decoding, that is, the noise reduction and amplifying circuits do not work during the test, and the pure tones are played directly to the transmitter after decoding.

Figure 7:
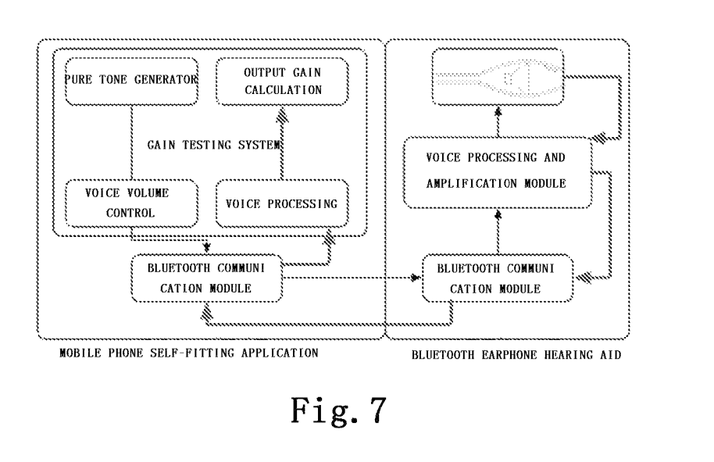
FIG. 7 is a schematic diagram of a gain test performed by a gain testing module according to an embodiment of the present invention.

Further specific embodiments, the gain testing module is included, as shown in FIG. 7. Its process is similar to the pure tone test, the difference is that there is only a pure tone signal generated by the pure tone generator, and it is a frequency scanning signal, after being the voice volume control and via a Bluetooth communication module, is sent to the hearing earphone's the Bluetooth communication module. The voice processing and amplifying module including the amplifying circuit and noise reduction and other voice processing do not work while the scanning, the test microphone at the front end of the microphone starts recording, and then the voice is encoded (Bluetooth supports CELT and AAC, but other encoding formats can also be used) and is sent through Bluetooth protocol to the mobile phone self-fitting application, is restored as recorded voice after voice processing. Output Gain Calculation is performed to determine the gain of the system. The gain test requires the calibration data of the hearing earphones (that is, the configuration information of the hearing earphones) provided in the background. The calibration data of the hearing earphones is measured on the manufacturing production line during its production and stored on the backend cloud server.

Figure 8:
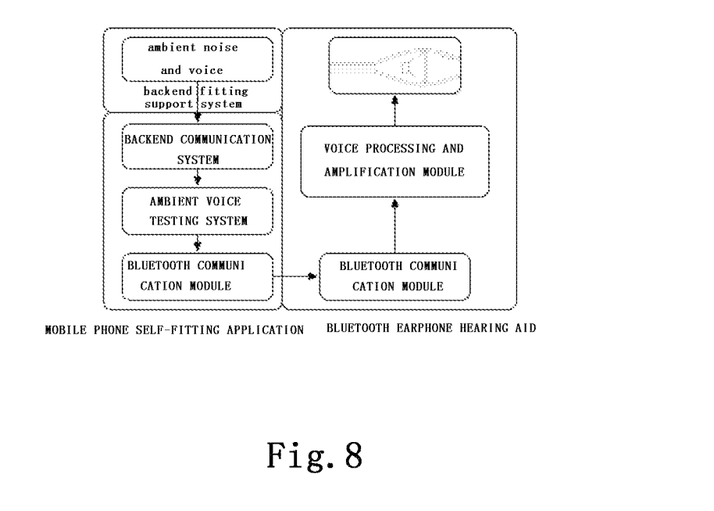
FIG. 8 is a schematic diagram of an ambient voice testing module performing an ambient voice test according to an embodiment of the present invention.

In a further specific embodiment, the ambient voice testing module, as shown in FIG. 8, obtains the test voice in a quiet environment and the test voice in a different noise environment by requesting the server in the cloud. The two-channel voice data simulates the actual voice field. The voice is received through the Bluetooth communication module of the hearing earphone, and is played to the user after being processed by the voice processing and amplification module, which is used to adjust the amplification and compensation gain value parameters in different scenarios.

In addition, the hearing earphone control module can control the hearing earphone test, that is, send control instructions, such as the instruction to enter the test state, the instruction to record the earphone at the front end of the transmitter, and to turn on and off the functions of the voice processing and amplification module instructions.

Figure 9:
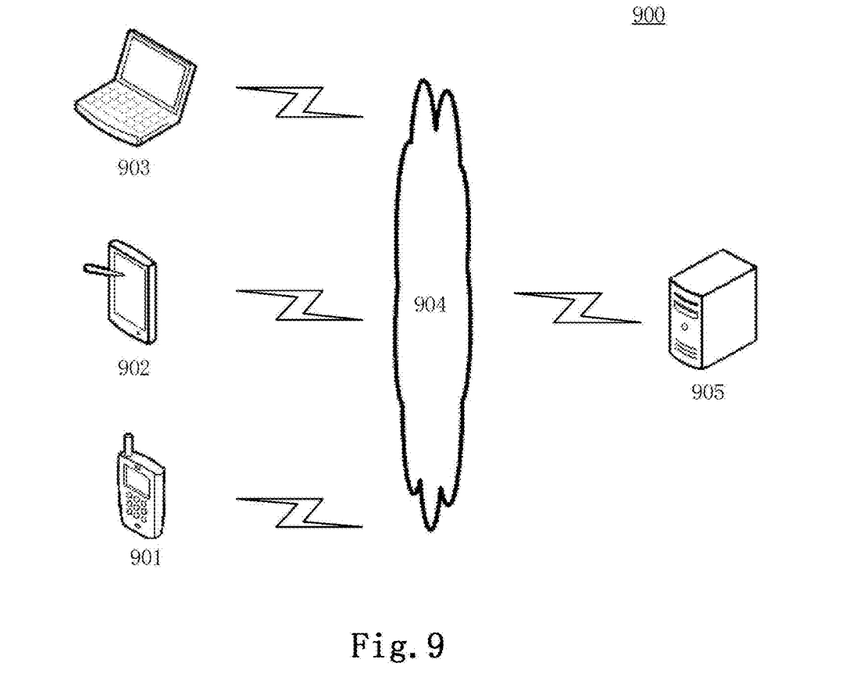
FIG. 9 is an exemplary system architecture diagram to which an embodiment of the present invention may be applied.

FIG. 9 shows an exemplary system architecture 900 of a fitting method or a fitting apparatus for a hearing earphone to which embodiments of the present invention can be applied.

As shown in FIG. 9, the system architecture 900 may include terminal devices 901, 902, and 903, a network 904 and a server 905. The network 904 is a medium used to provide a communication between the terminal devices 901, 902, 903 and the server 905. Network 904 may include various connection types, such as wired, wireless communication, or fiber optic cables, etc.

The user can use the terminal devices 901, 902, 903 to interact with the server 905 through the network 904 to receive or send messages and the like. Various communication client applications may be installed on the terminal devices 901, 902 and 903, such as shopping applications, web browser applications, search applications, instant messaging tools, email clients, social network software, etc (only for examples).

The terminal devices 901, 902, 903 may be various electronic devices having fitting screens for hearing earphones and supporting web browsing, including but not limited to smart phones, tablet computers, laptops and desktop computers, and the like.

The server 905 may be a server that provides various services, such as a backend management server that supports the e-commerce websites in the cloud browsed by the terminal devices 901, 902, and 903 by the user (just an example). The background management server can analyze and process the received product information query request and other data, and feedback the processing results (such as target push information, product information—just an example) to the terminal device.

It should be noted that the fitting method for the hearing earphone provided by the embodiment of the present invention is generally performed by the server 905, and accordingly, the computing device is generally set in the server 905.

It should be understood that the numbers of terminal devices, networks and servers in FIG. 9 are merely illustrative. There can be any number of terminal devices, networks, and servers according to implementation needs.

Figure 10:
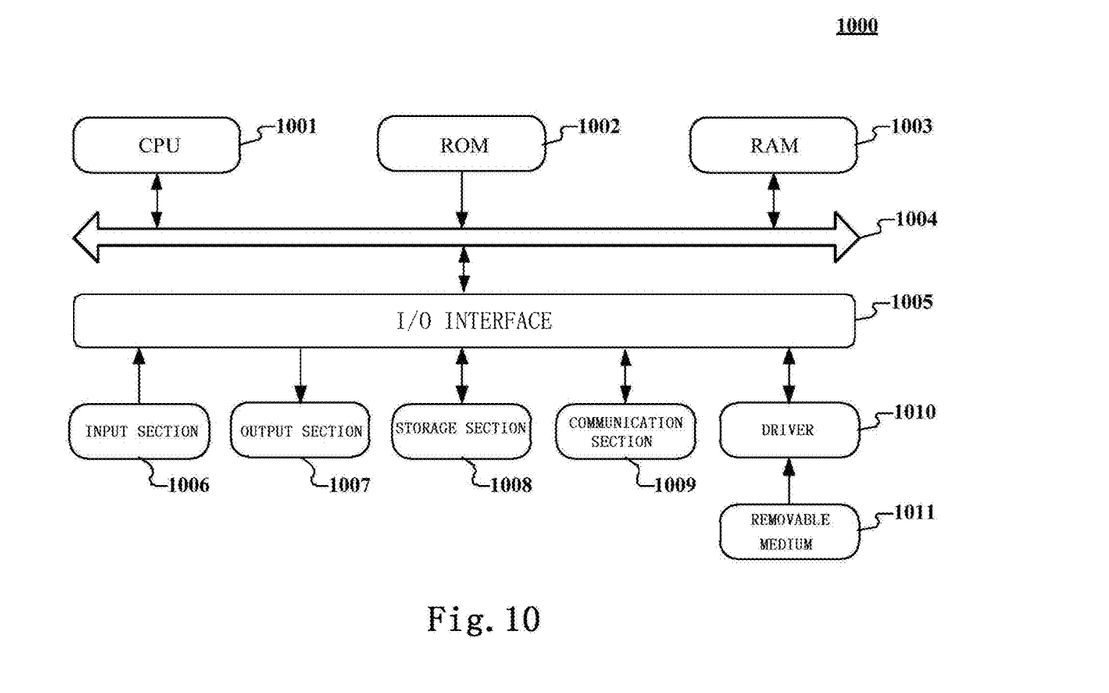
FIG. 10 is a schematic structural diagram of a computer system suitable for implementing a terminal device or a server according to an embodiment of the present invention.

Referring to FIG. 10 below, it shows a schematic structural diagram of a computer system 1000 suitable for implementing a terminal device according to an embodiment of the present invention. The terminal device shown in FIG. 10 is only an example, and should not impose any limitations on the functions and scope of use of the embodiments of the present invention.

As shown in FIG. 10, a computer system 1000 includes a central processing unit (CPU) 1001 that can be loaded into a random access memory (RAM) 1003 according to a program stored in a read only memory (ROM) 1002 or a program from a storage section 1008 Instead, various appropriate actions and processes are performed. In the RAM 1003, various programs and data necessary for the operation of the computer system 1000 are also stored. The CPU 1001, the ROM 1002, and the RAM 1003 are connected to each other through a bus 1004. An input/output (I/O) interface 1005 is also connected to the bus 1004.

The following components are connected to the I/O interface 1005: an input section 1006 including a keyboard, a mouse, etc.; an output section 1007 including a cathode ray tube (CRT), a liquid crystal fitting (LCD) for hearing earphones, etc., and a speaker, etc.; A storage section 1008 of a hard disk or the like; and a communication section 1009 including a network interface card such as a LAN card, a modem, and the like. The communication section 1009 performs communication processing via a network such as the Internet. A drive 1010 is also connected to the I/O interface 1005 as needed. A removable medium 1011, such as a magnetic disk, an optical disk, a magneto-optical disk, a semiconductor memory, etc., is mounted on the drive 1010 as needed so that a computer program read therefrom is installed into the storage section 1008 as needed.

In particular, the processes described above with reference to the flowcharts may be implemented as computer software programs in accordance with the disclosed embodiments of the present invention. For example, embodiments disclosed herein include a computer program product comprising a computer program carried on a computer-readable medium, the computer program containing program code for performing the methods illustrated in the flowcharts. In such an embodiment, the computer program may be downloaded and installed from the network via the communication portion 1009, and/or installed from the removable medium 1011. When the computer program is executed by the central processing unit (CPU) 1001, the above-described functions defined in the system of the present invention are executed.

It should be noted that the computer-readable medium shown in the present invention may be a computer-readable signal medium or a computer-readable storage medium, or any combination of the above two. The computer-readable storage medium can be, for example, but not limited to, an electrical, magnetic, optical, electromagnetic, infrared, or semiconductor system, apparatus or device, or a combination of any of the above. More specific examples of computer readable storage media may include, but are not limited to, electrical connections with one or more wires, portable computer disks, hard disks, random access memory (RAM), read only memory (ROM), erasable Programmable read only memory (EPROM or flash memory), optical fiber, portable compact disk read only memory (CD-ROM), optical storage devices, magnetic storage devices, or any suitable combination of the above. In the present invention, a computer-readable storage medium may be any tangible medium that contains or stores a program that can be used by or in conjunction with an instruction execution system, apparatus, or device. In the present invention, however, a computer-readable signal medium may include a data signal propagated in baseband or as part of a carrier wave, carrying computer-readable program code therein. Such propagated data signals may take a variety of forms, including but not limited to electromagnetic signals, optical signals, or any suitable combination of the foregoing. A computer-readable signal medium can also be any computer-readable medium other than a computer-readable storage medium that can transmit, propagate, or transport the program for use by or in connection with the instruction execution system, apparatus, or device. Program code embodied on a computer readable medium may be transmitted using any suitable medium including, but not limited to, wireless, wire-line, optical fiber cable, RF, etc., or any suitable combination of the foregoing.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code that contains one or more logical functions for implementing the specified functions executable instructions. It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It is also noted that each block of the block diagrams or flowchart illustrations, and combinations of blocks in the block diagrams or flowchart illustrations, can be implemented in special purpose hardware-based systems that perform the specified functions or operations, or can be implemented using A combination of dedicated hardware and computer instructions is implemented.

The modules involved in the embodiments of the present invention may be implemented in a software manner, and may also be implemented in a hardware manner. The described modules can also be provided in the processor, for example, it can be described as: a processor includes a pure tone testing module and a gain testing module. Herein, the names of these modules do not constitute a limitation on the module itself under certain circumstances.

As another aspect, the present invention also provides a computer-readable medium, which may be included in the device described in the above embodiments; or may exist alone without being assembled into the device. The above-mentioned computer-readable medium carries one or more programs, and when the above-mentioned one or more programs are executed by a device, the device includes obtaining the test result of user's hearing thresholds, so as to transmit the test result of hearing thresholds to the server, and then receive the test result of hearing thresholds. The first target compensation gain value of each of frequency bands calculated by the earphone configuration information; the generated pure tone signal is sent to the hearing earphone to receive the voice information after the pure tone signal is played, and then the gain data of each of frequency bands is adjusted to approach the corresponding first target compensation gain value. As well as being able to perform further refined tests on the user's hearing and make corresponding gain adjustments and compensations.

According to the technical solutions of the embodiments of the present invention, the problems of low fitting efficiency and reliability and high cost of existing hearing earphones can be solved.

The above-mentioned specific embodiments do not constitute a limitation on the protection scope of the present invention. It should be understood by those skilled in the art that various modifications, combinations, sub-combinations and substitutions may occur depending on design requirements and other factors. Any modifications, equivalent replacements and improvements made within the spirit and principle of the present invention shall be included within the protection scope of the present invention.

The invention claimed is:

1. A fitting method for a hearing earphone, including:
   obtaining, with a software application executed on a user device, a hearing threshold of a user;
   transmitting, with the software application, the hearing threshold to a server;
   obtaining, with the software application from the server, target compensation gain values of each of a plurality of frequency bands calculated based on configuration information of the hearing earphone and the hearing threshold;
   generating, with the software application, pure tone signals;
   sending, with the software application, the generated pure tone signals to the hearing earphone to play the generated pure tone signals;
   receiving, with the software application, sound detected in an ear canal by an inner ear microphone built in the hearing earphone so as to receive feedback information after playing the pure tone signals; and
   adjusting, with the software application based on the feedback information, gain value data of each of the plurality of frequency bands to approach corresponding target compensation gain values.

2. The method according to claim 1, further including:
   sending, with the software application, different types of first sound signals in a first environment to the hearing earphone to play the different types of first sound signals wherein, the different types of first sound signals are a combination of sounds at different frequency points;
   receiving, with the software application, sound detected in the ear canal by the inner ear microphone so as to receive selected type information from the user after playing the different types of first sound signals;
   recurrently, with the software application until a confirmation instruction is received, re-adjusting the gain value data after adjustment at each of the plurality of frequency bands based on the selected type information, selecting the re-adjusted gain value data at one of plurality of frequency bands as output gain data, and sending the output gain data to the hearing earphone.

3. The method according to claim 2, further including:
   sending, with the software application, second sound signals under each of a plurality of different second environments to the hearing earphone for playing the second sound signals under each of the plurality of different second environments in a manner where the gain values of high frequency, of medium frequency, or of low frequency respectively are adjusted, and receiving sound detected in the ear canal by the inner ear microphone built in the hearing earphone after playing the second sound signals under each of the plurality of different second environments;
   receiving, with the software application, a selected manner of adjustment for each of the plurality of different second environments; and
   recurrently, with the software application until a confirmation instruction is received, adjusting the re-adjusted gain value data of each of the plurality of frequency bands based on the selected manner of adjustment, selecting the re-adjusted gain value data of one of the plurality of frequency band as the output gain data, and sending the output data to the hearing earphone.

4. The method according to claim 3, further including:
   sending, with the software application, a data request to the server, and
   obtaining, with the software application from the server, the first sound signals under the first environment or the second sound signals under each of the plurality of second different environments.

5. The method according to claim 1, further comprising, before obtaining the hearing threshold, generating a pure tone signal and a narrow-band noise signal by a pure tone generator and a narrow band noise generator, respectively;
   synthesizing the pure tone signal and the narrow-band noise signal, and setting a preset volume, and
   sending the pure tone signal and the narrow-band noise signal to the hearing earphone to play the pure tone signal and the narrow-band noise signal to obtain the hearing threshold.

6. The method according to claim 1, wherein sending the generated pure tone signals to the hearing earphone includes:
   encoding the generated pure tone signal, and
   sending the encoded pure tone signal to a Bluetooth communication module in the hearing earphone, and
   wherein receiving the feedback information includes:
   receiving the feedback information encoded by the Bluetooth communication module.

7. A fitting device for a hearing earphone, including:
   one or more processors;
   a storage device configured to store one or more programs,
   the one or more programs, when executed by the one or more processors, are configured to:
   obtain a hearing threshold, and
   transmit the hearing threshold to a server,
   receive target compensation gain values of each of a plurality of frequency bands calculated based on the hearing threshold and configuration information of the hearing earphone, send pure tone signals to the hearing earphone to play the generated pure tone signals, and receive sound detected in an ear canal by an inner ear microphone built in the hearing earphone so as to receive feedback information after playing the pure tone signals, and adjust, based on the feedback information, gain value data of each of the plurality of frequency bands to approach corresponding target compensation gain values.

8. The device according to claim 7, wherein the one or more programs, when executed by the one or more processors, are further configured to:

send different types of first sound signals information in a first environment to the hearing earphone to play the different types of first sound signals information, receive sound detected in the ear canal by the inner ear microphone built in the hearing earphone after playing the different types of first sound signals so as to receive selected type information from the user, wherein, the different types of first sound signals are a combination of sounds at different frequency points, and recurrently, until a confirmation instruction is received, re-adjust the gain value data after adjustment at each of the plurality of frequency bands based on the selected type information, select the re-adjusted gain value data at one of the plurality of frequency bands as output gain data, and send the output gain data to the hearing earphone.

9. A non-transitory computer-readable medium, on which a computer program is stored, wherein, the program, when executed by at least one processor, implements the method according to claim 1.

* * * * *